(12) United States Patent
Calladine

(10) Patent No.: US 12,295,956 B2
(45) Date of Patent: May 13, 2025

(54) ANTI-VIRAL COMPOSITIONS

(71) Applicant: Calladine Pharmaceuticals Limited, Worcestershire (GB)

(72) Inventor: Daniel Calladine, Worcestershire (GB)

(73) Assignee: Calladine Pharmaceuticals Limited, Worchester (GB)

( * ) Notice: Subject to any disclaimer, the term of this patent is extended or adjusted under 35 U.S.C. 154(b) by 832 days.

(21) Appl. No.: 17/296,299

(22) PCT Filed: Nov. 28, 2019

(86) PCT No.: PCT/EP2019/082850
§ 371 (c)(1),
(2) Date: May 24, 2021

(87) PCT Pub. No.: WO2020/109442
PCT Pub. Date: Jun. 4, 2020

(65) Prior Publication Data
US 2022/0016124 A1 Jan. 20, 2022

(30) Foreign Application Priority Data
Nov. 29, 2018 (GB) ...................... 1819418

(51) Int. Cl.
| | | |
|---|---|---|
| *A61K 31/522* | (2006.01) | |
| *A61K 8/27* | (2006.01) | |
| *A61K 9/00* | (2006.01) | |
| *A61K 47/10* | (2017.01) | |
| *A61K 47/26* | (2006.01) | |
| *A61K 47/44* | (2017.01) | |
| *A61K 47/46* | (2006.01) | |
| *A61P 31/22* | (2006.01) | |
| *A61Q 17/04* | (2006.01) | |

(52) U.S. Cl.
CPC .............. *A61K 31/522* (2013.01); *A61K 8/27* (2013.01); *A61K 9/0014* (2013.01); *A61K 47/10* (2013.01); *A61K 47/26* (2013.01); *A61K 47/44* (2013.01); *A61K 47/46* (2013.01); *A61P 31/22* (2018.01); *A61Q 17/04* (2013.01)

(58) Field of Classification Search
None
See application file for complete search history.

(56) References Cited

U.S. PATENT DOCUMENTS 4,615,633 A  10/1986  Ser et al.

FOREIGN PATENT DOCUMENTS

| BE | 1022817 B1 * | 9/2016 | |
| EP | 948332 B1 * | 9/2003 | ........... A61K 31/522 |
| RU | 2093140 | 10/1997 | |
| RU | 2282473 | 8/2006 | |
| WO | WO 1998/018472 | 5/1998 | |
| WO | WO 2008/019213 | 2/2008 | |
| WO | WO 2008/045479 | 4/2008 | |
| WO | WO 2008/115776 | 9/2008 | |
| WO | WO 2008/122242 | 10/2008 | |
| WO | WO 2013/077881 | 5/2013 | |

* cited by examiner

Primary Examiner — Nannette Holloman
(74) Attorney, Agent, or Firm — Neil D. Gershon

(57) ABSTRACT

A solid or semi-solid state anti-viral lip balm composition comprising a direct or indirect nucleoside analog inhibitor of herpes simplex viral DNA polymerase or a pharmaceutically acceptable salt thereof mixed with at least one wax, at least one carrier oil selected from the group consisting of coconut oil including refined coconut oil and sunflower oil and a butter or butter substitute as a softening agent.

15 Claims, No Drawings

ANTI-VIRAL COMPOSITIONS

FIELD OF THE INVENTION

The present invention relates to an anti-viral composition, in particular a topical pharmaceutical composition for the therapeutic treatment or prevention of the herpes virus, especially herpes labialis.

BACKGROUND

The herpes simplex virus, also known as HSV, is an infection that causes herpes. There are two types of the herpes simplex virus, HSV-1 or oral herpes and HSV-2, or genital herpes. The most common symptoms of the HSV-1 virus are cold sores and fever blisters (herpes labialis) around the mouth and on the face. Herpes is a common virus that, although annoying & painful, does not normally lead to serious health issues. However, once a person has the virus, it remains in their skin and therefore that person will suffer from repeated outbreaks of cold sores throughout their life. Depending upon the individual, these outbreaks can be frequent and severe.

Several anti-viral compounds have been identified for either the systemic treatment of the viral infection or for topical application to the skin, such as penciclovir, ganciclovir, idoxurdine, cidofovir, foscarnet and aciclovir. It is desirable to treat cold sores topically rather than systematically and aciclovir, a HSV nucleoside analogue DNA polymerase inhibitor, tends to the antiviral agent of choice. This is applied as a cream to the infected areas of the skin during an attack. Ideally, the cream should be applied at the first sign of a cold sore, generally when a tingling sensation is experienced, but often the treatment is applied too late to have full effect.

Aciclovir is very difficult to formulate into a suitable cream or ointment for topical application because it has poor solubility in water and is almost totally insoluble in hydrophobic solvent systems. Therefore, it has proven problematic to provide a topical formulation that passes sufficiently quickly through the skin to the affected area at the onset of an attack prior to any significant skin cell disruption. Generally, the active aciclovir ingredient is provided in an oil-in-water topical formulation comprising a dispersed oil phase and a continuous aqueous phase containing the water and solubilised antiviral compound. GB Patent No. 1523865 first discussed the use of aciclovir and its salts as an anti-viral agent in the late 1970s and provided a topical ointment or cream containing an oil-in-water composition having 5% w/w aciclovir and up to 5% w/w propylene glycol.

There have been many attempts made since GB Patent No. 1523865 to provide an improved formulation for the topical application of aciclovir that increases its absorption into the skin and/or reduces its irritability to the skin. EP 1044543 found that increasing the amount of propylene glycol from 5% w/w to at least 30% w/w in the oil-in-water formulation increased absorption of the antiviral active ingredient, as did the addition of glycerol formal (EP 0662819) or diethylene glycol monoethyl ether (WO 97/34607).

WO 00/01390 describes how the addition of a sucrose ester into the formulation improved the absorption of, and tolerance to, aciclovir. The formulation included 0.1% to 10% w/w aciclovir, 0.1% to 40% w/w sucrose ester, from 20% to 40% w/w of water incorporated into a mixture with an oily phase. In particular, the inclusion of sucrose ester enabled the formulation to include smaller amounts of propylene glycol which has a dehydrating action on the skin.

EP 1741425 discusses a formulation that is suitable for application as a spray. The formulation contains 20-80% demineralised water together with the active ingredient, a solvent, solubilizing agent, a humectant, an anti-itching agent and an anti-oxidant.

The vast majority of the prior art topical formulations for the application of aciclovir are an ointment or cream. The most widely used cold sore cream is that sold under the brand name Zovirax™. Each gram of ZOVIRAX Cream, 5% contains 50 mg of acyclovir together with various inactive ingredients: cetostearyl alcohol, mineral oil, poloxamer 407, propylene glycol, sodium lauryl sulfate, water, and white petrolatum. The recommended dosage is to apply the cream five times per day for four days, with therapy being initiated as early as possible following the onset of signs of a cold sore. Prolonged use is not recommended due to the formulation being harsh to the skin, causing dry and cracked lips which in itself can lead to reactivation of the virus. The fingertip application of the cream to an infected area may also lead to virus transmission through the fingertips. This may be particularly serious if the user rubs their eyes following application of the cream. Lipstick applicators have been previously disclosed, for example in WO 98/18472 but their compositions were not satisfactory for use.

The prior art antiviral formulations are extremely good for short-term treatment of herpes labialis once an outbreak has occurred. However, the formulations do not prevent an outbreak and are not suitable for long term, continuous use. This is problematic when an outbreak often occurs without warning, frequently at the most inconvenient times, such as when a person goes on a holiday and is subject to extreme temperatures or high sun exposure. Outbreaks also often occur when a person is ill or under the weather. The application of the aciclovir cream may then be too late, serving only to reduce the severity of the outbreak rather than preventing it.

It is the aim of the present invention to provide an improved anti-viral formulation for topical application that overcomes, or at least alleviates, the abovementioned drawbacks.

SUMMARY OF THE INVENTION

According to a first aspect of the present invention there is provided a solid or semi-solid anti-viral lip balm composition comprising a direct or indirect nucleoside analog inhibitor of herpes simplex viral DNA polymerase or a pharmaceutically acceptable salt thereof mixed with at least one wax selected from the group consisting of beeswax, lanolin, paraffin wax, carnauba wax, candelilla wax, soy wax and ouricury wax, at least one carrier oil selected from the group consisting of white mineral oil, tamanu oil, olive oil, jojoba oil, calendula oil, canola oil, castor oil, almond oil, coconut oil, hydrogenated coconut oil, caprylic/capric triglyceride (derived from coconut oil and glycerine), grapeseed oil, corn oil, soybean oil, avocado oil, sunflower oil, pomegranate seed oil and hemp seed oil and a softening agent selected from a butter or butter substitute.

Preferably, the active ingredient is a direct nucleoside analog inhibitor of herpes simplex viral DNA polymerase selected from the group consisting of aciclovir, gancociclovir, valciclovir, penciclovir, idoxurdine, cidofovir and foscarnet, more preferably aciclovir.

The anti-viral active ingredient is mixed with a wax and at least one carrier oil, preferably two carrier oils and a softening agent. The provision of the antiviral active ingredient aciclovir within the wax, carrier oils and softening agent provides a solid or semi-solid formulation that can be applied to the skin to assist in the prevention of cold sores.

Preferably, the wax has a melting point of at least 40° C., preferably at least 60° C. The wax is a lipophilic, malleable solid near ambient temperatures. In a preferred embodiment the wax is beeswax or a mixture of beeswax with candelilla wax.

The carrier oil is liquid at ambient temperature and is mixed with the melted wax prior to addition of the active ingredient. The mixture with active ingredient added to it is then allowed to solidify to form the solid or semi-solid formulation. Preferably, at least one of the carrier oils is coconut oil, hydrogenated coconut oil, caprylic/capric triglyceride (derived from coconut oil and glycerine), a caprylic/capric/myristic/stearic triglyceride and/or sunflower oil.

The softening agent preferably comprises a butter or butter substitute selected from the group consisting of kokum butter, shea butter (butyrospermum parkii butter), cocoa butter, coconut butter, mango butter, a caprylic/capric/myristic/stearic triglyceride and caprylic/capric triglycerides (derived from coconut oil and glycerine).

Preferably, shea butter is used. Alternatively, a shea butter substitute may be used, such as a caprylic/capric triglyceride (derived from coconut oil and glycerine), such as that sold under the trade name Softisan 378®.

It is to be appreciated that the formulation should be of a solid or semi-solid consistency for durable application to the skin. As such the water content of the formulation should be kept to a minimum. Preferably, the maximum water content of the composition is less than 5%, more preferably less than 2%, especially less than 1%, ideally 0%.

Preferably, the lip balm softens from a relatively hard solid to a softer balm at 30-40° C., preferably 32-38° C.

In a preferred embodiment of the formulation an emulsifying agent is included to assist in complete dispersion of the active ingredient within the formulation. Preferably, lanolin or glycerine is included to assist in emulsification of the active ingredient for mixing with the wax and oil. The lanolin may also act as a surfactant as well as an emulsifying agent. If lanolin allergy is a problem, a lanolin substitute may be used, such as Softisan® 649. In alternative embodiments, a second or third emulsifying agent may be included in the formulation to aid dispersion of the ingredient, such as for example lanolin and/or Polysorbate 80. Optionally, emollient ingredients may be included to help soften the skin, for example octyldodecanol.

The formulation may include other optional ingredients which may be tailored to a particular end use. For example, the composition may include zinc oxide, titanium oxide, diethylamino hydroxybenzoyl hexyl benzoate, or ethylhexyl methoxycinnamate to provide a formulation with sunscreen. Further ingredients may include flavourings, scents, anti-inflammatory agents or colourings.

In a preferred formulation the lip balm includes an antioxidant, preferably being butylated hydroxytoluene (BHT).

Preferably, the composition consists essentially of aciclovir or a pharmaceutically acceptable salt thereof, beeswax, at least two carrier oils selected from sunflower oil and a caprylic/capric triglyceride (derived from coconut oil and glycerine) and at least one butter selected from a caprylic/capric/myristic/stearic triglyceride or shea butter. Other ingredients may be included in minor amounts.

A preferred embodiment of the lip balm consists essentially of the following:
aciclovir;
butylated hydroxytoluene;
Beeswax;
Sunflower oil;
a caprylic/capric triglyceride (derived from coconut oil and glycerine);
shea butter; and
lanolin.

It is preferable for the composition to provide a ratio of wax to oil from 1:3 to 1:5. The active antiviral agent is preferably included in a concentration of 0.1-10% w/w, preferably 3-5% w/w.

Preferably, the wax is provided in the range 20-33.3% w/w, more preferably about 25% w/w and the carrier oil including the softening agent being provided in the range 66.6-80% w/w based on total weight of the composition, more preferably about 75%.

Ideally, the lip balm comprises approximately one-quarter wax, half carrier oil and a quarter butter or butter substitute. Preferably, the lip balm includes a first carrier oil, a second carrier oil and a butter, each being provided in substantially the same amounts.

A second aspect of the present invention provides a lip balm according to the first aspect of the present invention for use in the prevention or reduction in the onset of herpes labialis.

Preferably, the use according to the second aspect of the present invention comprises administering the composition to an area of skin prone to herpes labialis at least once daily for a period of at least one week for the suppression of the herpes virus.

More preferably, the use may comprise administering the composition to an area of skin prone to herpes labialis at least twice daily for a period of at least one month for the suppression of the herpes virus, optionally increasing the administration to up to five times daily for a period of five days in times of physical or emotional stress.

BRIEF DESCRIPTION

The invention will now be illustrated by way of example only to the following Examples 1 to 6 detailing different solid-state anti-viral compositions according to embodiments of the present invention.

DETAILED DESCRIPTION

The present invention provides a topical solid or semi-solid formulation for the anti-viral agent aciclovir comprising at least aciclovir or a pharmaceutically acceptable salt thereof mixed with a wax and carrier oils to provide a solid or semi-solid formulation at ambient temperature. More preferably the anti-viral agent is mixed with a wax substance and at least two carrier oils with minimal water content to provide a balm formulation that may be applied to the skin, in particular the lip area, to reduce or prevent outbreaks of herpes labialis. It has surprisingly been found that the formulation allows for sufficient absorption of the active ingredient over time into the skin so as to reduce or prevent the occurrence of a cold sore, despite the formulation having a minimal water content. Furthermore, the balm is significantly less irritating to the skin so may be used at regular intervals to maintain good condition of the lips while serving to prevent an outbreak of herpes labialis. This is a major advantage over the prior art formulations which should only be applied following the onset of prodromal symptoms or signs of a cold sore for 5 days initially and for no more than 10 days in total, without prolonged usage due to the formulations being harsh to the skin, such that they can cause flaking, drying, cracking, irritation and soreness.

Generally, the formulation of Examples 1 to 5 of the present invention comprises 3 parts carrier oil, 1 part wax and 1 part butter, together with aciclovir (0.1-10% w/w) and optional other ingredients. However, it is to be appreciated that the particular amounts of the various ingredients may be adjusted depending upon the type of oil, wax and butter used in the formulation and depending on the consistency, flavour and texture desired in the finished formulation. In Example 6, the preferred embodiment of the present invention, the formulation is approximately one quarter wax, to two-quarter carrier oil and 1 quarter butter, with a small amount of lanolin as an emulsifying agent and butylated hydroxytoluene as antioxidant.

Example 1: Basic Solid-State Anti-Viral Composition According to One Embodiment of the Present Invention A solid-state anti-viral composition according to an embodiment of the present invention was made by placing beeswax, a white mineral carrier oil and solid kokum butter into a container and heating the container in a medium-to-low heat water bath to melt the ingredients together.

The melted ingredients were then removed from the heat and 5% aciclovir was added to the mixture with stirring to disperse the aciclovir throughout the composition. The composition was then allowed to solidify to form the solid-state anti-viral formulation.

Particulars of the composition were as follows:
Wax: Beeswax BP grade (10 g)
Carrier oil: White mineral oil BP grade (30 ml)
Butter: Shea butter (5 ml)
Active ingredient: Aciclovir (2 g. approx. 5% w/w)

The solid-state formulation was applied daily to the lip area of a person who was prone to regular herpes labialis outbreaks for a period of one week prior to sun exposure and also subsequently during sun exposure. No outbreak occurred. However, the dispersion of aciclovir was found to be limited in this formulation.

Example 2: An Alternative Embodiment of a Solid-State Anti-Viral Composition According to the Present Invention A solid-state anti-viral composition was made according to the method of Example 1 but with additional ingredients to improve the consistency and application of the formulation.
Particulars of the composition were as follows:
Wax: Beeswax BP grade (10 g)
Carrier oil: White mineral oil BP grade and tamanu oil (30 ml)
Butter: Shea butter (5 ml)
Active ingredient: Aciclovir (2 g. approx. 5% w/w)
  Glycerin BP grade (5 ml)
The formulation of Example 2 was effective against an outbreak of herpes labialis in a similar manner to that of Example 1 but was found to have a better consistency and feel for application to the skin. The glycerine assisted in the dispersion of the aciclovir throughout the formulation.

Example 3: A Third Embodiment of a Solid-State Anti-Viral Composition According to the Present Invention A solid-state anti-viral composition was made according to the method of Example 1 but with different basic ingredients as follows:
Wax: Lanolin (10-25%) and beeswax (5 g)
Carrier oil: Castor oil
Butter: Kokum butter BP grade (5 ml)
Active ingredient: Aciclovir (2 g. approx. 5% w/w)

Example 4: A Fourth Embodiment of a Semi-Solid Anti-Viral Composition According to the Present Invention A solid-state anti-viral composition was made according to the method of Example 1 with the same basic ingredients but additional minor ingredients to provide flavour, sun protection and anti-inflammatory properties as follows:
Wax: Beeswax BP grade (10 g)
Carrier oil: White mineral oil BP grade and tamanu oil (30 ml)
Butter: Kokum butter BP grade (5 ml)
Active ingredient: Aciclovir (2 g. approx. 5% w/w)
Emulsifying agent: Glycerin BP grade (5 ml)
Flavouring: Vanilla extract
Anti-inflammatory agent: Tea tree oil (few drops).
Sunscreen: Zinc oxide.

Example 5: A Fifth Embodiment of a Solid-State Anti-Viral Composition According to the Present Invention A solid-state anti-viral composition according to an embodiment of the present invention was made by gentle heating of beeswax with a mixture of oils, butter and other ingredients, including 5% aciclovir (as detailed below) to provide around 60 ml of a pourable hot liquid.

The liquid was then poured into several 2-5 ml applicator lip balm tubes or a lip balm tin and allowed to cool, thus solidifying the contents. The aciclovir is known to be relatively heat stable and so does not de-nature during this process.
Wax: Beeswax BP grade (15 g)
Carrier oil: Sunflower oil (oleic acid) (15 ml)
  Castor oil (5 ml)
Butter: Shea butter (10 ml)
Active ingredient: Aciclovir (2.5 g; approx. 5% w/w)
Emulsifying agent: Glycerine (5 ml)
  Lanolin (10 ml)
  Polysorbate 80 (1 drop)
The addition of the three emulsifying agents glycerine, lanolin and polysorbate 80 improved the solubility and dispersion of the active ingredient in the formulation.

Example 6: A Sixth Embodiment of a Solid-State Anti-Viral Composition According to the Present Invention A solid-state anti-viral composition according to a preferred embodiment of the invention was made from substantially one quarter wax, two-quarter carrier oil and one-quarter butter, a small amount of lanolin used as an emulsifier and an antioxidant BHT, as shown below. The blend of the wax with 2 carrier oils and a butter acting as a softening agent achieved the desired product consistency and softening point so that the balm easily spreads on the lips without being too hard and without being too soft to avoid breaking on application, and also extrudes from the tube easily without breaking or sticking. The below formulation was found to provide a tackiness that allowed for suitable transfer of material on to the lips, and the formulation is retained on the lips for a longer duration to give adequate time for the active pharmaceutical ingredient aciclovir to absorb.

| Substance | Amount | Specification | Function |
|---|---|---|---|
| Aciclovir | 5% weight by weight | PHEur | Active ingredient |
| Butylated hydroxytoluene (BHT) | 0.02% by weight | BP/PHEur | Antioxidant |
| Yellow beeswax (cera alba) | 36 g | BP/PhEur 6.0, BP, FCC | Solidifying agent |
| Sunflower oil (refined) | 40 ml | BP/PhEur | Carrier oil |
| Myglyol ® 812 | 40 ml | PhEur | Carrier oil |
| Shea butter, refined (pressed) (Butyrospermum Parkii), refined organic | 40 g | — | Softening agent. |
| Lanolin | 8 g | BP/PH•Eur 9.5 | Emulsifying agent |

All the above ingredients except the aciclovir and BHT were melted, mixed and cooled slightly to about 60-80° C. being careful to still maintain liquid form. Aciclovir and BHT were added to the mixture which was stirred for at least 1 minute, preferably at least 3 minutes and poured into a lip balm filling tray pre-loaded with 50 slimline lip balm tubes each with a volume of 2 ml and allowed to cool. Excess overspill from the tops of the tubes were scraped off with a spatula and the tubes were then capped.

The lip balm was then used at the onset of prodromal symptoms or at the early onset of vesicular lesion, with treatment continued for 5 days at 5 times per day. The lip balm is applied to the lip area in a small circular motion at a rate of 1-2 full circle cycles per second (medium pace) over the lesion and surrounding tissue for around 10 seconds to allow adequate transfer of the balm. During this process there is a small amount of softening of the lip balm in contact with the skin which aids transfer of the material.

The lip balm was found to work effectively to prevent a full outbreak while maintaining the healthy condition of the lips.

In an alternative embodiment, the shea butter may be substituted with an equivalent amount of Softisan® 378 from IOI Oleo GmbH. This a caprylic/capric/myristic/stearic triglyceride of vegetable origin. With its low melting point, it leaves a non-tacky and non-greasy film on the skin.

The specific ingredients making up the lip balm play an important role in providing satisfactory application of the active ingredient to the sensitive lip area while conditioning the lips to prevent drying and cracking of the skin. The beeswax is the solidifying agent which is less shiny than other types of waxes, providing a balm with less gloss and less slip. This results in the balm being less visible when applied to the skin which may be particularly desirable for male users. It also creates a sufficiently solid product such that it can be provided in stick form and extended from a packaging tube for application and assists in the stability of the product at room temperature.

The sunflower oil, Miglyol 812 and shea butter also impart important properties to the lip balm. The sunflower oil is less greasy than many oils and has no unpleasant taste or smell. It is also one of the only oils available in high grade pharmaceutical EP form and has minimal water content. Miglyol 812 is a carrier oil with moisturising properties and no unpleasant smell or taste. The shea butter helps stabilize the melting point of the balm and allows it to exist in a solid state at room temperature for ease of use, but which also allows the balm to soften slightly upon application to the skin and to turn from a relatively hard solid to a softer solid, and melts a little, which aids absorption of the ingredients. Alternatively, Softisan® 378 may be used as a substitute for shea butter. Additionally, lanolin is used for emulsification properties and as a surfactant to obtain the correct dispersion of the ingredients throughout the balm and the antioxidant BHT prevents oxidation and reduces rancidification of the oils and fats contained in the formulation. The end result is a stable, moisturising balm that is solid at room temperature but slightly softens at skin temperature during application to aid transfer of the material.

The lip balm according to the present invention provides a product at just the right softness to be applied comfortably and effectively, sticks to the lips without being greasy, and provides prolonged adherence whilst moisturising and locking in moisture to the lips to help protect and nourish the lips, and ensuring adequate transfer of the anti viral agent. If the balm was too hard, applying it to the lips could be painful or tear the delicate blisters that occur during cold sore infection. However, if it is not hard enough the balm would melt in you your pocket, or not extrude correctly from the lip balm tube.

Ideally, the product is provided in a long, thin tube with a removable cap, the base of the tube having actuation means to lift some the product beyond the top of the tube for use. Preferably, the tube is opaque white plastic but could also be fully or partly transparent so that a user will know when the product is low and acquire more lip balm before running out. A 2-3 ml volume tube will supply 2-3 g of the balm which is enough for a 5 day course at 5× per day. This slim line lip balm tubing also provides a product with a smaller diameter than conventional non-medicated lip balms, enabling more focused application of the product. However, larger tubes or wider tubes holding more product may be provided for longer, preventative use. It is clear that the ability to apply the product directly to an infected area without the use of the fingertips may help prevent spread of infection.

It is to be appreciated that an unlimited number of different formulations may be made based on the basic formula according to the present invention. For example, a mixture of beeswax and candililla wax may be used to harden the product, or Kokum butter substituted for shea butter to make the product less soft, which would help maintain the correct consistency if being used in warmer ambient temperatures. Any desired flavouring may be included in minor amounts, as may ingredients to provide scent, healing and/or soothing properties.

One or a number of essential oils may be included such as, for example, peppermint, orange, line, lemon, vanilla, grapefruit, camphor, tea tree oil, raspberry oil, lavender oil and rose oil. Desired herbs may also be infused into the carrier oil, prior to mixing with the wax and butter. Suitable herbs include but are not limited to calendula, lemon balm, chamomile, plantain, rose petals and violet leaves.

The formulations according to the present invention are a significant advance away from those anti-viral formulations containing aciclovir according to the prior art in that they have minimal water content, are in a solid or semi-solid state and yet surprisingly allow for sufficient absorption of the antiviral agent over time to prevent or reduce an outbreak of herpes labialis. The formulation is much kinder to the skin and therefore can be applied to the skin at regular intervals for significant lengths of time, thereby enabling the formulation to be used as a preventative measure before any signs of an outbreak occur. This has the added advantage of a user being able to apply the formulation in advance of a period of increased risk, such as the individual being exposed to conditions that will usually result in an outbreak, for example before holidays or times of stress.

The formulations according to the present invention have also been found to provide greater accumulation of the active ingredient in the dermal skin layer. This is in contrast to the prior art topical formulations that are mainly concentrated in the epidermis with only a small concentration penetrating into the deeper dermal layer. It appears that the ability to apply a formulation that remains on the skin for longer periods and may be applied more frequently for a longer duration, allows for a build-up of the anti-viral agent in the dermal skin layer which may prevent or significantly reduce the incidence of cold sores occurring in an individual.

While it is not possible to prevent infection with the herpes simplex virus, the lip balm according to the present invention provides a significant step towards preventing the spread of infection and suppressing outbreaks of cold sores. As a treatment, the balm should be applied five times daily at approximately four hourly intervals, preferably as early as possible (prodrome or erythema stage) for at least five days. For each application the lip balm should be rubbed on to the affected area of lips or skin for 5-10 seconds, or more if required to enable a softening of the product and to allow a satisfactory transfer of a viable amount of the product to the skin to then allow sufficient absorption of the active ingredient to occur.

The gentle conditioning properties of the composition enable the balm to be used in a regular, preventative manner. This represents a significant improvement over topical applications which are often applied too late to completely stop a cold sore. The present invention may be applied twice daily to the entire lip area for a number of months or even continuously to help reduce the incidence of cold sores. If the user is at increased risk of developing a cold sore, such as if developing cold/flu-like symptoms, at times of physical or emotional stress, exhaustion or high UV exposure, application may be increased to a maximum of 5× per day for short periods. If the user is immunocompromised for the long term the application can continue at 5× day longer term. The composition of the lip balm will not dry the lips or cause them to crack, which is a common problem with traditional aciclovir white cream water-in-oil solutions when these are used beyond a typical 5 day treatment period.

The invention claimed is:

1. A solid or semi-solid state anti-viral lip balm composition comprising a direct or indirect nucleoside analog inhibitor of herpes simplex viral DNA polymerase selected from the group consisting of aciclovir, gancociclovir, valciclovir, penciclovir, idoxurdine, cidofovir and foscarnet or a pharmaceutically acceptable salt thereof mixed with beeswax and two carrier oils selected from the group consisting of coconut oil, sunflower oil, and caprylic/capric triglycerides derived from coconut oil and glycerine and a softening agent selected from a shea butter or a shea butter substitute, the composition having a maximum water content of less than 2%, the composition comprising beeswax in the range 20-33.3% w/w and wherein the first and second carrier oils are provided in substantially equal amounts.

2. A solid or semi-solid state anti-viral lip balm as claimed in claim 1 wherein the DNA polymerase inhibitor is acyclovir.

3. A lip balm as claimed in claim 1 wherein the coconut oil is a refined coconut oil comprising caprylic/capric triglycerides.

4. A lip balm as claimed in claim 1 wherein shea butter is a shea butter substitute comprising caprylic/capric/myristic/stearic triglyceride.

5. A lip balm as claimed in claim 1 wherein the maximum water content of the composition is less than 1%.

6. A lip balm as claimed in claim 1 further comprising an antioxidant.

7. A lip balm as claimed in claim 1 further comprising at least one of zinc oxide, titanium oxide, diethylamino hydroxybenzoyl hexyl benzoate and ethylhexyl methoxycinnamate.

8. A lip balm as claimed in claim 1 further comprising an emulsifying agent selected from the group consisting of glycerine, lanolin, Bis-Diglyceryl Polyacyladipate-2 and polysorbate 80.

9. A lip balm according to claim 1 wherein the carrier oils with the softening agent is provided in the range 66.6-80% w/w based on total weight of the composition.

10. A lip balm according to claim 9 wherein the lip balm comprises approximately one-quarter beeswax, half carrier oil and a quarter shea butter or shea butter substitute, the first carrier oil, a second carrier oil and a butter, each being provided in substantially the same amounts.

11. A lip balm according to claim 1 consisting essentially of:
   beeswax;
   shea butter or caprylic/capric/myristic/stearic triglyceride;
   Triglycerides;
   Sunflower oil;
   Lanolin or Bis-Diglyceryl Polyacyladipate-2; and
   butylated hydroxytoluene.

12. A lip balm according to claim 1 for use in the prevention or reduction of the onset of herpes labialis.

13. A lip balm for use according to claim 12 wherein the composition is administered to an area of skin prone to herpes labialis at least once daily for a period of at least one week for the suppression of the herpes virus.

14. A lip balm for use according to claim 12 wherein the composition is administered to the lip area twice daily for up to one year, or indefinitely to reduce the incidence of a cold sore.

15. A lip balm for use according to claim 12 wherein the composition is administered to the lip area twice daily for up to one year, or indefinitely to reduce the incidence of a cold sore and wherein application of the balm is increased to a maximum of 5 times per day during a period of increased risk of cold sores due to physical and/or emotional stresses.

* * * * *